United States Patent [19]

Donetti et al.

[11] Patent Number: 5,047,410

[45] Date of Patent: Sep. 10, 1991

[54] INDOLYL DERIVATIVES AND THEIR USE AS 5-HT$_3$, RECEPTOR ANTAGONISTS

[75] Inventors: Arturo Donetti, Milan; Marco Turconi, Voghera; Massimo Nicola, Pavia; Rosamaria Micheletti, Milan, all of Italy

[73] Assignee: Istituto De Angeli S.p.A., Milan, Italy

[21] Appl. No.: 378,958

[22] Filed: Jul. 12, 1989

[30] Foreign Application Priority Data

Jul. 12, 1988 [IT] Italy ............................ 21330 A/88

[51] Int. Cl.$^5$ ............... A61K 31/165; A61K 31/235; A61K 31/275; A61K 31/38; A61K 31/405; A61K 31/44; A61K 31/18; C07D 221/22; C07D 215/38; C07C 233/64

[52] U.S. Cl. ..................... 514/299; 514/210; 514/212; 514/339; 514/419; 514/311; 514/342; 514/314; 514/343; 514/346; 514/350; 514/359; 514/406; 514/428; 514/443; 514/521; 514/523; 514/534; 514/535; 514/540; 514/617; 514/618; 514/619; 514/621; 514/622; 540/480; 540/602; 548/492; 548/259; 548/359; 548/569; 546/112; 546/183; 546/273; 546/156; 546/169; 546/170; 546/275; 546/291; 546/298; 546/316; 546/318; 560/12; 560/13; 560/20; 560/22; 560/23; 560/37; 560/38; 560/39; 560/41; 564/162; 564/163; 564/166; 564/167; 564/169; 564/170; 564/176; 564/183; 564/186

[58] Field of Search ............... 548/492; 514/419, 299, 514/339, 210, 212; 546/112, 183, 273; 540/480, 602

[56] References Cited

U.S. PATENT DOCUMENTS 4,814,345 4/1989 Ohlendorf et al. ............... 548/492

Primary Examiner—Johann Richter

[57] ABSTRACT

New pharmacologically active amidino and guanidino derivatives which are 5-HT$_3$ receptor antagonists useful as antiemetic, gastric prokinetic and antimigrainic agents of the following general formula (I)

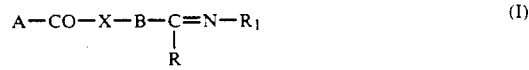

, wherein the substituents are defined hereinbelow, which compounds are 5-HT$_3$ receptor antagonists useful as antiemetic gastric prokinetic and antimigraine agents, inter alia.

8 Claims, No Drawings

INDOLYL DERIVATIVES AND THEIR USE AS 5-HT₃, RECEPTOR ANTAGONISTS

The present invention relates to novel pharmacologically active amidino and guanidino derivatives, to the process for their preparation and to the pharmaceutical compositions containing them. The new compounds are 5-HT₃ receptor antagonists useful as antiemetic, gastric prokinetic and antimigraine agents.

Serotonin (5-HT) is known to play a major role both in the central nervous system (CNS) and in peripheral nervous system (PNS). Furthermore it is known that there are different subtypes of receptors for 5-HT; the receptors which have been emphasized on the nervous terminations are called neuronal 5-HT receptors or M-receptors or 5-HT₃ receptors (B. P. Richardson, G. Egel "Trends in Neurological Sciences" 1986, 424). Compounds acting as 5-HT₃ receptor antagonists may be effectively used in the prevention and treatment of migraine, cluster headaches and trigeminal neuralgia. Since these compounds may have a beneficial role on gastrointestinal motility, a further use of these compounds is in delayed gastric emptying, dyspepsia, flatulence, gastroesophageal reflux, peptic ulcer, constipation and irritable bowel syndrome. It has been also discovered that some 5-HT₃ antagonists may be particularly useful in the treatment of chemotherapy or radiation induced nausea and emesis (J. R. Fozard "Trends in Pharmacological Sciences" 8, 44 1987).

The patent applications GB 2,125,398 A, EP 223 385, EP 254 584, EP 067 770 and U.S. Pat. No. 3,177,252 describe for these uses esters or amides derivatives of substituted heterocyclic or arylic acids, having as substituent of carboxylic acid a basic chain, generally azabicycloalkanic.

We have now synthesized, and this is the object of the present invention, a novel class of structurally distinct compounds showing specific 5-HT₃ receptor blocking activity, surprisingly superior to the one of the known compounds, object for example of the above mentioned patent applications. These new compounds may be useful for the treatment of chemotherapy and radiation induced nausea and emesis and/or delayed gastric emptying. They may be also of value in the treatment of arrhytmia, motion sickness, migraine, cluster headaches, trigeminal neuralgia, anxiety, stress psychical illness and psychoses. Moreover they may be used in gastrointestinal motility disorders such as dyspepsia, flatulence, oesophageal reflux, peptic ulcer, constipation, irritable bowel syndrome and ipokinesia, and also in arrhytmia and in rhinitis.

The compounds object of the present invention have the general formula (I)

$$A-CO-X-B-\underset{R}{C}=N-R_1 \qquad (I)$$

wherein
A is a group selected from substituted benzene

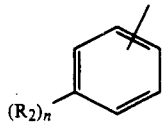

(a)

R₂ is H, C₁₋₆ alkyl, C₁₋₆ alkoxy optionally substituted by halogen, hydroxy, acetyl, or R₂ is C₁₋₆ alkeniloxy, C₁₋₆ alkynyloxy, halogen, amino, C₁₋₆ alkylamino, nitro, sulphonylamino and n is 0-4 or mono- or bicyclic heterocycle selected from

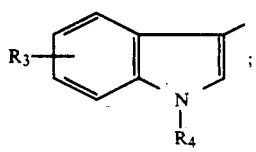

(b)

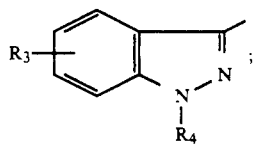

(c)

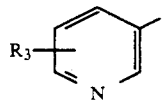

(d)

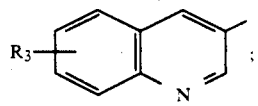

(e)

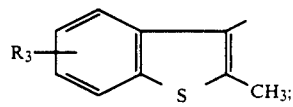

(f)

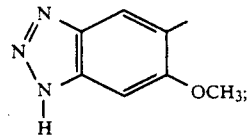

(g)

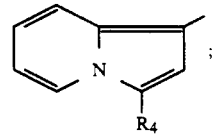

(h)

wherein
R₃ is H, halogen, C₁₋₆ alkoxy
R₄ is H, C₁₋₆ alkyl
X represents —O— or —NH—
B is a group selected from

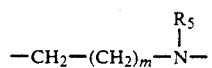

(a)

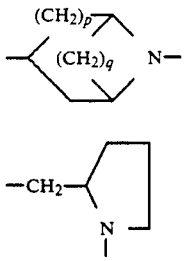

-continued (b)

(c)

wherein
m is 1, 2
p is 0, 1, 2,
q is 0, 1, 2, 3
$R_5$ is H, $C_{1-6}$ alkyl

R represents H, $C_{1-6}$ alkyl optionally substituted by halogen, $NR_6R_7$ in which $R_6$ is H, $C_{1-6}$ alkyl, $NO_2$, CN and $R_7$ is H, $C_{1-6}$ alkyl; and $R_1$ represents H, $C_{1-6}$ alkyl optionally substituted by halogen, or CN.

For the pharmaceutical use the compounds of general formula (I) are used as such or under the form of physiologically compatible acid addition salts. The term "acid addition salts" includes salts with inorganic or organic acids. Physiologically compatible acids used for the salification, include, for example, maleic, citric, tartaric, fumaric, methansulphonic, hydrochloric, hydrobromic, sulphuric, nitric, acetic, benzoic, ascorbic and phosphoric acids. The compounds of general formula (I) and their physiological acceptable salts may also exist as physiological acceptable solvates, such as hydrates, which constitute a further feature of the present invention. Although the double bond in the amidine radical is indicated in general formula (I) as present in a particular position, other tautomeric forms are also possible. The present invention includes therefore such tautomeric forms as regards both the compounds and the processes of their preparation.

Some of the compounds of formula (I), according to the present invention, contain chiral or prochiral centers and thus they may exist in different stereoisomeric forms including enantiomers of (+) and (−) type, diastereoisomers or mixture of them. The present invention includes therefore both the individual isomers and the mixture thereof. It has to be understood that, when mixtures of optical isomers are present, they may be separated according to the classic resolution methods based on their different physicochemical properties, e.g. by fractional crystallization of their acid addition salts with a suitable optically active acid or by the chromotographic separation with a suitable mixture of solvents.

In the present invention the term A of formula (a) means preferably 2-alkoxy-4-amino-5-halobenzene, 2-alkoxy-5-sulphonamidobenzene, 2-alkoxy-4-amino-5-nitro-benzene or 2-metoxy-4-alkylamine-5-halobenzene. The term halogen means fluorine, chlorine, bromine or iodine. The &term A of formula (b) means 3-linked indole, the one of formula (c) means 3-linked indazole, the one of formula (d) means 3-linked pyridine, the one of formula (e) means 3-linked quinoline, the one of formula (f) means 3-linked 2-methylbenzothiophene, the one of formula (g) means 5-linked 6-methoxy-1H-benzotriazole and the one of formula (h) means 3-linked indolizine. The group B of formula (b) means 3-linked 8-azabicyclo[3.2.1]octane, 3-linked 9-azabicyclo[3.3.1]nonane, 2-linked 7-azabicyclo[2.2.1]eptane or 4-linked piperidine. It has to be understood that in the compounds of general formula (I) the azabicyclic moieties of the group B of formula (b) may be endo or exo substituted. Compounds of general formula (I) containing the pure endo or exo moieties may be prepared starting from the appropriate precursors or by separating the mixtures of the endo or exo isomers not stereospecifically synthesized by conventional methods, such as e.g. chromatography. The endo substitution is preferred.

The compounds of general formula (I) may be prepared by reacting a compound of general formula (II)

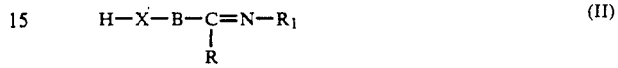

wherein X, B, R and $R_1$ are as hereinbefore defined, optionally in the form of its acid addition salts, with a reactive compound of formula (III)

wherein A is as hereinbefore defined and Y is a leaving group such as chlorine, imidazolyl, OCOAlk (where Alk is methyl optionally substituted by fluorine or ethyl), or OH. When Y is OH the reaction is carried out in the presence of suitable condensing agents such as dicyclo-hexylcarbodiimide (DCC). The reaction may be conveniently carried out in aprotic solvents such as methylene dichloride, chloroform, dimethylformamide, tetrahydrofurane, dioxane, toluene at a temperature ranging from 0° to 130° C., preferably for 0° to 60° C. The presence of an acid acceptor, such as triethylamine or pyridine may be beneficial in some cases. In other cases the presence of a strong base such as sodium hydride or 1,8-diazabicyclo[5.4.0]undec-7-ene (DBU) may be advantageous.

Compounds of general formula (II), used as starting material in the above process, may be obtained by reacting compounds of formula (IV)

wherein X and B are as hereinbefore defined, and P is hydrogen or protecting group, with compounds of formula (V)

wherein R and $R_1$ are as hereinbefore defined, and Z is leaving group such as $C_{1-4}$ alkoxy, $C_{1-4}$ alkylthio, halogen, phenoxy. The compounds of formula (V) may be in the form of addition salts with organic or mineral acids such as hydrochloric, hydrobromic, idroiodic, sulphuric, nitric, tetrafluoboric, alklsulphonic, arylsulphonic, thiocianic acid, preferably hydrochloric and sulphuric acid. The reaction may be conveniently carried out in a polar solvent such as methanol, ethanol, acetonitrile, acetone, ethylacetate, dimethylformamide, dimethylsolphoxide, water or mixtures of them at a temperature ranging from 10° to 120° C., preferably from 25° to 80° C. The protecting groups P may be, for example, acetyl, benzoyl, carbobenzyloxy, p-nitrocarbobenzyloxy, benzyl, 2,4-dimetoxybenzyl, benzhydryl, trityl, and they may be removed by conventional methods, for example by catalytic or transfer hydrogenation, acid or basic hydrolysis. The compounds of formula (II) in which X and B are as hereinbefore defined, R is $NH_2$ and $R_1$ is H, may be obtained by reacting compounds of formula (IV) with cyanamide.

The reaction may be carried out without solvent or in water, ethanol, at a temperature ranging from 70° C. to melting temperature of the mixture.

The compounds of formula (II) in which X, B and R are as hereinbefore defined, and R is H, may be obtained by reacting compounds of formula (VI)

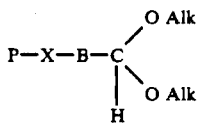  (VI)

wherein P, X, B, Alk are as hereinbefore defined, with amines of formula (VII)

$H_2N-R_1$  (VII)

wherein $R_1$ is as hereinbefore defined. The reaction may be conveniently carried out in an inert solvent such as methylene dichloride, chloroform, benzene, toluene, acetonitrile, diethyl ether, dioxane, tetrahydrofurane or without solvent, at a temperature ranging from: $-10°$ to 80° C., preferably from 0° to 40° C. The intermediates of formula (VI) may be prepared by reacting compounds of formula (IV) and dimethylformamide dialkylacetale. The reaction may be conveniently carried out in an inert solvent, such as methylene dichloride, diethyl ether, tetrahydrofurane, dioxane, benzene, toluene, acetonitrile chloroform or without solvent at a temperature ranging from 0° to 110° C., preferably from 20° to 60° C.

The compounds of formula (II) in which X, B and R are as hereinbefore defined and R is H may also be prepared by desulphurizing thioureas of formula (VIII)

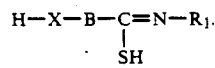  (VIII)

The reaction may be carried by Nickel Raney or by $H_2O_2$ in an appropriate solvent such as methylene dichloride, chloroform, methanol, ethanol, water or mixtures of them, at a temperature ranging from 10° to 70° C., preferably at room temperature. The thioureas of formula (VIII) may be obtained by reacting a compound of formula (IV) with ammonium thiocyanate or with an isothiocyanate of formula (IX)

$R_1-N=C=S$  (IX)

wherein $R_1$ is as hereinbefore defined. The reaction may be conveniently carried out in solvents such as water, methanol, ethanol, tetrahydrofurane, acetone or benzenene at a temperature from 25° to 100° C., preferably from 40° to 80° C.

The compounds of general formula (II) in which X, B and $R_1$ are as hereinbefore defined, and R is $NR_6R_7$ may be prepared by reacting compounds of formula (X)

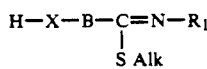  (X)

wherein X, B, Alk and $R_1$ are as hereinbefore defined, with an amine of formula (XI)

$HNR_6R_7$  (XI)

wherein $R_6$ and $R_7$ are hereinbefore defined. The reaction may be carried out in polar solvents such as methanol, ethanol, isopropanol, water, dimethylformamide or mixtures of them at a temperature ranging from 0° and 100° C., preferably at room temperature. The compounds of formula (X) may be obtained from the compounds of formula (IV) and dithioalkylamido carbonates of formula (XII)

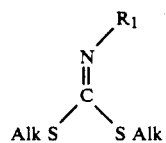  (XII)

The reaction may be carried out in polar solvents such as methanol, ethanol, isopropanol, water, dimethylformamide or mixtures of them at a temperature from 0° to 100° C., preferably at room temperature.

The compounds of general formula (I) may be also prepared by reacting a reactive compound of general formula (V) with a compound of general formula (XIII)

$A-CO-X-B-H$  (XIII)

wherein A, X and B are as hereinbefore defined, in a polar solvent, such as methanol, ethanol, acetonitrile, acetone, ethylacetate, dimethylformamide, dimethylsulfoxide, water or mixtures of them at a temperature ranging from 10° to 120° C., preferably from 25° to 80° C. The compounds of formula (V) may be in the form of addition salts with organic or mineral acids. The case in which R is $NH_2$ and $R_1$ is H, the same compounds may be obtained by reacting compounds of formula (XIII) with cyanamide in the presence of water, ethanol or without solvent at a temperature ranging from 70° to the melting temperature of the mixture.

The intermediates of formula (XIII) may be obtained by reacting a compound of formula (III) with a compound of formula (XIV) optionally as acid addition salt, $H-X-B-Q$  (XIV)

wherein X and B are as hereinbefore defined, and Q is H or a protecting group.

The protecting group Q may be benzyl, benzhydryl, vinyloxy carbonyl, benzyloxy carbonyl and it may be removed by conventional methods, such as catalytic or transfer hydrogenation, treatment with acids or bases. The reaction may be performed in solvents, such as methylene dichloride, chloroform, dimethylformamide, tetrahydrofurane, dioxane, toluene at a temperature ranging from 0° to 130°, preferably from 0° to 60° C. The presence of an acid acceptor such as triethylamine or pyridine may be advantageous in some cases as well as the presence of a strong base such as NaH or DBU.

The compounds of general formula (I), in which R is H, may be prepared by reacting an amine of formula (VII) with a compound of general formula (XV)

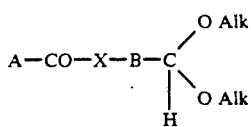

wherein A, X, B and Alk are as hereinbefore defined, in inert solvents, such as methylene dichloride, chloroform, benzene, toluene, acetonitrile, diethyl ether, dioxane, tetrahydrofurane or without solvents at a temperature ranging from $-10°$ to $80°$ C., preferably from $0°$ to $40°$ C.

The intermediates of formula (XV) are obtained by reacting a compound of formula (XIII) with dimethylformamide dialkylacetale in an inert solvent such as methylene dichloride, chloroform, diethyl ether, tetrahydrofurane, dioxane, benzene, toluene, acetonitrile or without solvent at a temperature ranging from $0°$ to $110°$ C., preferably from $20°$ to $60°$ C.

The compounds of general formula (I) in which R is H, may be also prepared by desulphurizing thioureas of formula (XVI)

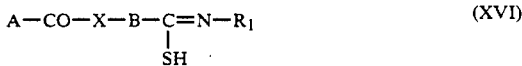

by Nickel Raney or by $H_2O_2$ in an appropriate solvent such as methylene dichloride, chloroform, methanol, ethanol, water or mixtures of them at a temperature ranging from $10°$ to $70°$ C., preferably at room temperature.

The intermediates of formula (XVI) may be obtained by reacting compounds of formula (XIII) with ammonium thiocyanate or with isothiocyanates of formula (IX) in solvents, such as water, methanol, ethanol, tetrahydrofuran, acetone at a temperature ranging from $25°$ to $100°$ C., preferably from $40°$ to $80°$ C.

The compounds of general formula (I) in which R is $NR_6R_7$ may be also prepared by reacting an amine of formula (XI) with a compound of formula (XVII)

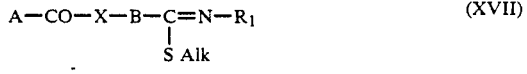

wherein A, X, B, Alk and $R_1$ are as hereinbefore defined. The reaction may be performed in polar solvents such as methanol, ethanol, isopropanol, water, dimethylformamide or mixtures of them at a temperature ranging from $0°$ and $100°$ C., preferably at room temperature. The compounds of formula (XVII) may be obtained by reacting the intermediates of formula (XII) and XIII) in polar solvents such as methanol, ethanol, isopropanol, water, dimethylformamide or mixtures of them at a temperature ranging from $0°$ and $100°$ C., preferably at room temperature.

It has to be understood that compounds of general formula (I) containing an A, R and R group which may give rise to another A, R and R' group are useful novel intermediates. Some of these transformations may also occur in the intermediates for compounds of general formula (I). Some examples of such conversion, which obviously do not include all possibilities, are:

1) A N-nitroguanidine may be transformed into a guanidine by reduction.

2) A heterocyclic N-H may be transformed into a N-alkyl group by alkylation.

3) A N-cyanoformamidinic group may be transformed into a N-alkylformamidinic group by reaction with an alkylamine.

4) N-cyanoguanidinic group may be transformed in guanidinic group by treatment with acids.

These transformations are well known to any chemist skilled in the art.

The compounds of formula (I) prepared according to the processes as above described may be optionally converted with inorganic or organic acids into the corresponding physiologically compatible acid addition salts for example by reacting with conventional methods the compounds as bases with a solution of the corresponding acid in a suitable solvent. Particularly preferred acids include for example hydrochloric, sulphuric, hydrobromic, acetic, citric, tartaric acids.

Preferred groups of compounds according to the present invention for their better activity as $5\text{-}HT_3$ receptor blocking agents are those formed by the compounds of general formula (I) in which:

—A is 2-methoxy-4-amino-5-chlorophenyl, B is the group (a), X is NH, R and $R_1$ are as above defined —A is 3-linked 1H-indol, 3-linked 1-methylindazol, 3,5-dimethylphenyl or 3,5-dichlorophenyl, B is the group (b), and X, R and $R_1$ are as above defined.

—A is 2-methoxy-4-amino-5-chlorophenyl, B is the group (c), X is NH, R and $R_1$ are as above defined.

As already mentioned hereinbefore the new compounds of formula (I), according to the present invention, have interesting pharmacological properties owing to their ability to antagonize the physiological 5-HT effects at $5\text{-}HT_3$ receptors in warm-blooded animals. Therefore the new compounds are commercially useful in the prevention and in the treatment of disorders wherein $5\text{-}HT_3$ receptors are involved, such as chemotherapy or radiation induced nausea and emesis, migraine, delayed gastric emptying, stress-induced psychological disorders, irritable bowel syndrome, arrhytmia and rhinitis.

The following test shows that the compounds, object of the present invention, have favorable characteristics in this respect.

PHARMACOLOGY

Bezold-Jarish reflex in anesthetized rats

Rats (250–275 g) were anesthetized with urethane (1.25 g/kg ip.). The blood pressure and the heart rate were recorded from the left femoral artery by means of a pressure transducer (Statham) connected with a cardiotachometer. The Bezold-Jarish reflex was elicited by rapid intravenous injection of serotonin (20 µg/kg).

Increasing doses of antagonists were injected 5 min. before serotonin to evaluate their effect on the initial bradycardia and associated fall in blood pressure resulting from the reflex vagal stimulation. In other experiments, the right vagus nerve was stimulated with platinum electrodes at 10 V, 10Hz, 2 msec, (Grass 248 stimulator), to evoke bradycardia. $ED_{50}$ values were calculated by linear regression analysis of the data expressed as percentage inhibition. The obtained potency of three compounds object of the present invention is shown below:

|  | Bradycardia<br>ED$_{50}$ ($\mu$g/kg$^{-1}$, i.v.) | Hypotension<br>ED$_{50}$ ($\mu$g/kg$^{-1}$, i.v.) |
|---|---|---|
| Compound 7 | 0.04 | 0.06 |
| Compound 15 | 0.2 | 0.5 |
| Compound 16 | 0.01 | 0.3 |

According to a further feature of the present invention there are provided pharmaceutical compositions comprising as active ingredient at least one compound of formula (I), as hereinbefore defined, or a physiologically compatible acid addition salt thereof in association with pharmaceutical carriers or excipients. For pharmaceutical administration the compounds of general formula (I) and their physiologically compatible acid addition salts may be incorporated into the conventional pharmaceutical preparations in either sold or liquid form. The compositions may, for example, be presented in a form suitable for oral, rectal or parenteral administration. Preferred forms include, for example, capsules, tablets, coated tablets, ampoules, suppositories and oral drops.

The active ingredient may be incorporated in excipients or carriers conventionally used in pharmaceutical compositions such as, for example, talc, gum arabic, lactose, gelatin, magnesium stearate, corn starch, aqueous or non-aqueous vehicles, polyvinylpyrrolidone, mannitol, semisynthetic glycerides of fatty acids, sorbitol, propylene glycol, citric acid, sodium citrate.

The compositions are advantageously formulated as dosage units, each dosage unit being adapted to supply a single dose of the active ingredient. Each dosage unit may conveniently contain from 5 mg to 100 mg and preferably from 10 mg to 50 mg of the above ingredient.

The following examples illustrate some of the new compounds according to the present invention, but they are not to be considered in any way limiting of the scope of the invention itself:

EXAMPLE 1

S-Methyl-N-cyano-(4-hydroxy)-piperidin-1-thiocarboxymidate

A solution of 4-hydroxypiperidine (3 g) in ethanol (10 ml) was added dropwise to a suspension of dithiomethylcyanoimidocarbonate (4.3 g) in ethanol (20 ml). The reaction mixture was stirred at room temperature for 24 hours, then the solvent was evaporated under nitrogen. Crystallization of the residue from ethyl acetate afforded the title compound (3.9 g). M.p. 90°-92° C.

Analogously the following intermediate was obtained:
S-Methyl-N-cyano-endo-(3-hydroxy)-8-azabicyclo[3.2.1]octan-8-thiocarboxymidate
M.p. 103°-105° C.

EXAMPLE 2

1-(N-Cyano-N',N'-dimethyl)guanyl-4-hydroxypiperidine

Dimethylamine (19 g) was added dropwise to a solution of S-methyl-N-cyano-(4-hydroxy)-piperidin-1-thiocarboxymidate (4 g) in ethanol (250 ml). The reaction mixture was stirred at room temperature for 4 days, then the solvent was degased by nitrogen and evaporated under vacuum. The residue was chromotographed on silica (eluent $CH_2Cl_2/CH_3OH$ 95:5). Thus the title compound was obtained (2.15 g). M.p. 103°-105° C.

Analogously the following intermediates can be obtained:
1-(N-Cyano-N'-methyl)guanyl-4-hydroxypiperidine M.p. 120° C. endo-8-(n-Cyano-N'-methyl)guanyl-8-azabicyclo[3.2.1]octan-3-ol. M.p. 130°-132° C.

EXAMPLE 3 endo-8-(N-Cyanoguanyl)-8-azabicyclo3.2.1loctan-3-ol

A suspension of endo-8-azabicyclo[3.2.1]octan-3-ol hydrochloride (2.0 g) and sodium dicyanamide (1.2 g) in n-butanol (6.25 ml) was heated at 140° C. for 2.5 hours. The reaction mixture was concentrated to dryness, the solid residue was taken up with water and the insoluble solid was collected by filtration. After washing accurately with water and after drying under vacuum 1.25 g of the desired product sufficiently pure were obtained. M.p. 197°-200° C.

EXAMPLE 4

N-Nitro-N'-aminoethylguanidine hydrochloride

To a solution of N-triphenylmethyl-1,2-diamino ethane (2 g) in methylene chloride/methanol 1:1 (40 ml) a suspension of 2-methyl-1(3)-nitro-2-pseudo-thiourea (0.9 g) in methylene chloride/methanol 1:1 (40 ml) was added. The resulting solution was stirred at room temperature for 24 hours. N-Nitro-N'-(2-triphenylmethylaminoethyl)guanidine, m.p. 229°-230° C. was obtained by filtration. The triphenylmethyl protection was removed by hydrolysis with hydrochloric acid in ethanol/water, yielding the desired compound (0.5 g), M.p. 217°-219° C.

EXAMPLE 5

1-(N',N'-Dimethylguanyl)-4-hydroxypiperidine hydrochloride

A solution of 1-(N-cyano-N',N'-dimethyl)guanyl-4-hydroxypiperidine (2.7 g) in 50% HCl (30 ml) was heated at 100° C. for 1 hour. The water was evaporated and the residue was freeze-dried obtaining the title compound which was used as such in the following reaction. M.p. 60°-65° C.

Similarly the following intermediates can be obtained: 1-(N-Methylguanyl)-4-hydroxypyrimidine. hydrochloride. M.p. 55°-60° C. endo-8-(N-Methylguanyl)-8-azabicyclo[3.2.1]octan-3-ol hydrochloride. M.p. 244°-245° C.

EXAMPLE 6 endo-8-guanyl-8-azabicyclo3.2.1loctan-3-ol hydrochloride

A mixture of endo-8-azabicyclo[3.2.1]octan-3-ol hydrochloride (10.0 g) and cyanamide (5.14 g) was heated with stirring for 3 hours at 120° C. and then allowed to cool. It was taken up with 30 ml of warm absolute ethanol, acidified with alcoholic HCl and the insoluble solid was collected by filtration. The desired product was crystalized from absolute ethanol. M.p.>270° C.

Analysis;
Found % C 46.72, H 7.86, N 20.601,
$C_8H_{15}N_3O \cdot HCl$;
Calc. % C 46.71, H 7.84.1, N 20.43.

Analogously the following intermediates can be obtained: endo-9-Guanyl-9-azabicyclo[3.3.1]nonan-3-ol hydrochloride. M.p. 186°–189° C. 2-Aminomethyl-1-guanylpyrrolidine hydrochloride.

EXAMPLE 7 endo-8-Imino methyl-8-azabicyclo[3.2.1]octan-3-ol hydrochloride

Ethyl formimidate hydrochloride (1.9 g), newly prepared, was added to a solution of endo-8-azabicyclo[3.2.1]octan-3-ol (2.0 g) in absolute ethanol (60 ml). The reaction mixture was stirred for 3 hours at room temperature, then some more ethyl formimidate were added (0.86 g) and stirring was continued for 3 hours. The reaction mixture was then allowed to stand at room temperature (r.t.) overnight. After concentration to dryness the obtained residue was chromatographed on Silicagel (eluent $CH_2Cl_2/CH_3OH/CH_3COOH/H_2O$ 80:20:10:2). After crystallization from a mixture of absolute ethanol and acetone 0.5 g of the desired product were obtained. A further crystallization gave a product with M.p. 177°–178° C.

EXAMPLE 8

1-(1'-Iminoethyl)-4-hydroxypiperidine hydrochloride 1.46 g of ethyl acetoimidate hydrochloride was added to a solution of 4-hydroxy-piperidine (1.0 g) in 10 ml of absolute ethanol. The resulting mixture was stirred at room temperature for 6 hours and then allowed to stand for 7 days. After concentration to dryness the obtained oil spontaneously solidified. After crystallization from acetone 0.7 g of the desired product were obtained.
M.p. 78°–80° C.

Analogously the following intermediate can be obtained: 1-(1'-Iminoethyl)-2-aminomethyl)-pyrrolidine hydrochloride.

EXAMPLE 9 endo-8-(N-Methylthiocarbamoyl)-8-azabicyclo[3.2.1]octan-3amine hydrochloride a) 1.5 g of endo-3-acetylamino-8-azabicyclo[3.2.1]octane hydrochloride was dissolved in methanol and passed through an IRA 400 resin column (OH form). After concentration of the fractions containing the desired product, 1.1 g of endo-3-acetylamino-8-azabicyclo[3.2.1]octane as a free base was collected and used directly for the following step.

b) 0.5 g of methylisothiocyanate in 50 ml ol tetrahydrofurane (THF) were added to a solution of endo-3-acetylamino-8-azabicyclo[3.2.1]octane (1.1 g) in THF (100 ml). After a few minutes of stirring the precipitation of white solid was noted. The stirring was kept on for 2 hours and then the solid was collected by filtration. 1.25 g of endo-3-acetylamino-8-(N-methyl thiocarbamoyl)-8-azabicyclo[3.2.1]octane obtained. M.p. 259°–260° C.

c) 1.2 g of endo-3-acetylamino-8-(N-methyl thiocarbamoyl)-8-azabicyclo[3.2.1]octane were hydrolized in 100 ml of 17% HCl at 100°–110° C. for 24 hours. The concentration to dryness of the reaction mixture gave 1.02 g of the desired product. M.p. 244°–245° C. The base can be obtained by conventional methods.

EXAMPLE 10 endo-(8-Azabicyclo[3.2.1]oct-3-yl)-3,5-dichlorobenzoate a) A solution of 3,5-dichlorobenzoylchlpride (11.8 g) and of endo-8-vinyloxy-carbonyl-8-azabicyclo[3.2.1]octan-3-ol (11.1 g) in pyridine (200 ml) was stirred at room temperature for 5 hours and then concentrated to dryness. The residue was taken up with ethyl acetate and the organic layer was washed with diluted HCl, with diluted NaOH and with water until neutrality. The raw product, so obtained, was crystallized from diisopropyl ether and then from acetonitrile. 11.4 g of endo-[8-vinyloxycarbonyl)-8-azabicyclo[3.2.1]oct-3-yl]-3,5dichlorobenzoate were obtained. M.p. 137°–138° C.

b) A solution of bromine (5.2 g) in methylene chloride (40 ml) was added dropwise, under stirring, to a solution of endo-[8-(vinyloxycarbonyl)-8-azabicyclo[3.2.1]oct-3-yl]-3,5-dichlorobenzoate (12.0 g) in the same solvent (200 ml) until the reddish-yellow color remained visible for some seconds. The reaction mixture was concentrated to dryness, taken up with methanol and refluxed for 30 minutes. After cooling the hydrobromide of the desired product was separated. M.p. 249°–250° C. (dec.). The base was obtained by conventional methods. 7.0 g M.p. 182°–184° C.

Analogously the following intermediate was obtained: endo-N-(9-Azabicyclo[3.2.1]non-3-yl)-1-methylindazol3-carboxamide hydrochloride. M.p. 151°–155° C.

EXAMPLE 11 endo-(8-Azabicyclo3.2.11oct-3-yl)-3,5-dimethylbenzoate

A suspension of endo-8-azabicyclo[3.2.1]octan-3-ol hydrochloride (3.5 g) and 3,5-dimethylbenzoylchloride (4.8 g) in 0-dichloro benzene was heated at 150°–160° C. for 3 hours until the stirring stuck. After cooling the residue was taken up with water and the acid aqueous layer was washed with ethyl acetate. After alkalization with 10% NaOH, the desired product was extracted with ethyl acetate. 2.7 g were obtained. M.p. 137°–138° C.

Analogously the following intermediates were obtained: endo-(9-Azabicyclo[3.3.1]non-3-yl)-1H-indol-3-carboxylate.
M.p. 230° C. (dec.)
endo-(8-Azabicyclo[3.2.1]oct-3-yl)-3-quinolinecarboxylate.
M.p. 199°–200° C
(Piperidin-4-yl)-3,5-dimethylbenzoate hydrochloride.
M.p. 214°–215° C.

EXAMPLE 12 endo-N-(8-Azabicyclo3.2.11oct-3-yl)-3,5-dimethylbenzoate a) 1.36 g of vinylchloroformate dissolved in benzene (20 ml) were added to a solution of endo-N-(8-methyl-8-azabicyclo[3.2.1]oct-3-yl)-3,5-dimethylbenzamide (3.5 g) in benzene (100 ml) cooled at 10° C. and under stirring. A white solid precipitated and the reaction mixture was heated at 60° C. for 20 hours and then allowed to cool. The reaction mixture was washed with diluted HCl and then the organic layer was acidified and concentrated to dryness. 1.9 g of endo-N-(8-vinyloxycarbonyl-8-azabicyclo[3.2.1]oct-3-yl)-3,5-dimethylbenzamide were obtained. M.p. 219°–220° C.

b) The desired product was prepared starting from endo-N-(8-vinyloxycarbonyl-8-azabicyclo[3.2.1]oct-3-yl)3,5-dimethylbenzamide in an analogous manner as described in example 10. M.p. 119°–120° C.

EXAMPLE 13

[1,(N-Cyano-N',N'-dimethyl)guanylpiperidin-4-yl]-3,5-dimethylbenzoate (Compound 1)

A solution of 3,5-dimethylbenzoic acid chloride (1.7 g) in $CH_2Cl_2$ (10 ml) was added dropwise to a solution of 1-(N-cyano, N', N'-dimethyl)guanyl-4-hydroxypiperidine (2 g) in $CH_2Cl_2$ (20 ml) and pyridine (1.2 ml). The reaction mixture was stirred at room temperature overnight. The solvent was evaporated and the residue, after taking up with ethyl acetate, was washed with acidic and basic water. After drying and evaporation the residue was chromotographed on silica (eluent $CH_2Cl_2$/ethyl acetate 8:2). Thus the title compound was obtained (0.8 g). M.p. 134° C.

Analysis;
Found % C 65.68, H 7.39, N 17.00,
$C_{18}H_{24}N_4O_2$;
Calc. % C 65.83, H 7.37, N 17.06.

EXAMPLE 14

4-Amino-5-chloro-2-methoxy-N-(N'-nitro-N''-aminoethylguanidino)benzamide (Compound 2)

A solution of 4-amino-5-chloro-2-methoxy benzoic acid (0.6 g) and N,N'-carbonyldiimidazole (0.49 g) in anhydrous dimethylformamide (DMF) (15 ml) was stirred at room temperature for 30 minutes, then a solution of N-nitro-N'-aminoethylguanidine hydrochloride (0.55 g) and 1,8-diazabicyclo[5.4.0]undec-7-ene (DBU) in DMF was added. The mixture was stirred for 4 hours at 50° C., then was cooled, poured into water and extracted with methylene chloride. The organic layer was washed with sodium carbonate solution and dried. After cooling, the title compound was collected as a solid, M.p. 226°-227° C. (dec.)

Analysis;
Found % C 40.02, H 4.55. N 25.39,
$C_{11}H_{15}ClN_6O_4$;
Calc. % C 39.951, H 4.5, N 25.41.

EXAMPLE 15 endo 8-(N-Cyanoguanyl)-8-azabicyclo3.2.1]oct-3-yl]-1H-indol-3-carboxylate (Compound 3)

Trifluoroacetic anhydride (0.26 g) was added, under stirring and at room temperature, to a solution of indole-3carboxylic acid (0.165 g) in 10 ml of THF and the reaction mixture was stirred for 10 minutes. endo-8-(N-Cyanoguanyl)8-azabicyclo[3.2.1]octan-3-ol (0.2 g) dissolved in THF (15 ml was then added. The reaction mixture was stirred at the same temperature for 2 hours, then was concentrated to dryness and taken up with ethyl acetate; after washing with a solution of sodium carbonate and water the organic layer was concentrated to dryness again. The residue was chromatographed on Silicagel (eluent $CH_2Cl_2/CH_3OH$ 93:7). 0.027 g of the desired compound were obtained. M.p. 145° C.

Analysis;
Found % C 63.814, H 5.5, N 19.91,
$C_{18}H_{19}N_5O_2$;
Calc. % C 64.08, H 5.67, N 20.76.

EXAMPLE 16 endo-[8-(N-Methylguanyl)-8-azabicyclo3.2.1]oct-3-yl]-1H-indole-3-carboxylate (Compound 4)

A suspension of 3-indolecarbonylchloride (0.6 g) and endo-8-(N-methylguanyl)-8-azabicyclo[3.2.1]octan-3-ol hydrochloride (0.5 g) in 0-dichlorobenzene (4 ml) was heated at 150°-160° C. for 1 hour. After cooling the obtained solid was collected by filtration and dichlorobenzene was removed. The solid was taken up with diluted HCl and washed with ethyl acetate; the aqueous layer was filtrated in the presence of carbon and concentrated to dryness again. After triturating with diethyl ether and freeze-drying 0.15 g of the desired product were obtained. M.p. 159°-160° C.

Analysis;
Found % C 58.83, H 6.52, N 15.49,
$C_{18}H_{22}N_4O_2·HCl$;
Calc. % C 59.58, H 6.39, N 15.44.

Analogously the following compound were obtained:

endo-(8-Guanyl-8-azabicyclo3.2.1]oct-3-yl)quinoline-3-carboxylate dihydrochloride (Compound 5)

M.p. 224°-225° C. (EtOH)
Analysis;
Found % C 53.40, H 5.78, N 13.90,
$C_{18}H_{20}N_4O_2·HCl$;
Calc. % C 54.4, H 5.58, N 14.10.

EXAMPLE 17 endo-(8-Guanyl-8-azabicyclo3.2.1]oct-3-yl)-3,5dichlorobenzoate hydrochloride (Compound 7)

A mixture of endo-(8-azabicyclo[3.2.1]oct-3-yl)-3,5-dichlorobenzoate (1 g), cyanamide (0.25 g) and $H_2O$ 50.1 ml) was heated at 110°-120° C. until melting. After heating for three hours and after a night at room temperature, the glassy mass was taken up with warm absolute ethanol obtaining a solid which was treated with alcoholic hydrochloric acid. After crystallization from isopropanol the title compound, as hydrochloride, was obtained (0.2 g). M.p. >260° C.

Analysis;
Found % C 47.42, H 4.75, N 11.41,
$C_{15}H_{17}Cl_2N_3O_2·HCl$;
Calc. % C 47.57, H 4.79, N 11.09.

Analogously the following compounds can be obtained:

endo-(9-Guanyl-9-azabicyclo3.3.1]non-3-yl)-3,5-dimethylbenzoate hydrochloride (Compound 6)

M.p. 249°-250° ($CH_3CN$)
Analysis;
Found % C 60.82, H 7.45, N 11.84,
$C_{18}H_{25}N_3O_2·HCl$;
Calc. % C 61.44, H 7.45, N 11.94.

endo-N-(9-Guanyl-9-azabicyclo[3.2.1]non-3-yl)-1-methylindazol-3-carboxamide hydrochloride (Compound 8)

4-Amino-5-chloro-2-methoxy-N-(2-guanidinoethyl)-benzamide hydrochloride (Compound 9)

4-Amino-5-chloro-2-methoxy-N-[2-(N-guanyl)-N-ethylamino]ethylbenzamide hydrochloride (Compound 10)

M.p. 186°-191° C.

4-Amino-5-chloro-2-methoxy-N-(1-guanylpyrrolidin-2-yl)methylbenzamide hydrochloride (Compound 11)

6-Methoxy-1H-benzotriazol-N-(2-guanidinoethyl)-5-carboxamide hydrochloride (Compound 12)

endo-(8-Guanyl-8-azabicyclo3.2.1]oct-3-yl)-3,5dimethylbenzoate hydrochloride (Compound 13)

M.p. 258°–260° C. (CH$_3$CN)
Analysis;
Found % C 59.71, H 7.07, N 12.03,
C$_{17}$H$_{23}$N$_3$O$_2$·HCl;
Calc. % C 60.43, H 7.16, N 12.44.

endo-(8-Guanyl-8-azabicyclo3.2.1]oct-3-yl)-1H-indol-3carboxylate hydrochloride (Compound 14)

M.p.>270° C.
Analysis;
Found % C 58.18, H 6.03, N 16.08,
C$_{17}$H$_2$ON$_4$O$_2$·HCl;
Calc. % C 58.53, H 6.07, N 16.06.

endo-8-(Iminomethyl-8-azabicyclo3.2.1]oct-3-yl)-1H-indol-3carboxylate hydrochloride (Compound 16)

M.p. 260° C. (dec) [EtOH/(iPr)$_2$O]
Analysis;
Found % C 60.87, H 5.98, N 12.53,
C$_{17}$H$_{19}$N$_2$O$_2$·HCl;
Clac. % C 61.16, H 6.04, N 12.59.

EXAMPLE 18 endo-(8-Iminomethyl-8-azabicyclo[3.2.1]oct-3-yl)-3,5-dichlorobenzoate hydrochloride (Compound 15)

Ethyl formimidate hydrochloride (0.43 g) was added portion wise to a suspension of endo-(8-azabicyclo-[3.2.1]oct-3-yl)-3,5-dichlorobenzoate (1 g) in ethanol (10 ml). The reaction mixture was stirred at room temperature for 2 hours, filtered and dried. The residue treated with warm CH$_2$Cl$_2$, gave the title product (0.45 g). M.p.>250° C.
Analysis;
Found % C 45.71, H 4.70, N 7.78,
C$_{15}$H$_{16}$Cl$_2$N$_2$Cl$_2$·HCl;
Calc. % C 45.94, H 4.71, N 7.70.

4-Amino-5-chloro-2-methoxy-N-2-(N-iminomethyl)-N-ethylamino]ethyl benzamide hydrochloride (Compound 17)

endo-8-(N-Cyanoimino)methyl-8-azabicyclo-[3.2.1]oct-3-yl]-1-indazole-3-carboxylate (Compound 18)

endo-N-8-(N-Cyanoimino)methyl-8-azabicyclo-3.2.1]oct-3-yl]-1 indole-3-carboxamide (Compound 19)

endo-[8-(N-n.Butilimino)methyl-8-azabicyclo-[3.2.1]oct-3-yl]1-indazole-3-carboxylate hydrochloride (Compound 20)

endo-N-(9-Iminomethyl-9-azabicyclo[3.3.1]non-3-yl)-1-methylindazole-3-carboxamide hydrochloride (Compound 21)

4-Amino-5-chloro-2-methoxy-N-[2-(N'-cyanoimino)-methyl]ethylamino benzamide (Compound 22)

M.p. 212°–217° C.
Analysis;
Found % C 48.61, H 4.80, N 23.70,
C$_{12}$H$_{14}$ClN$_5$O$_2$;
Calc. % C 48.74, H 4.77, N 23.68.

endo-(9-Iminomethyl-9-azabicyclo[3.3.1]non-3-yl)pyridine-3-carboxylate hydrochloride (Compound 23)

endo-(8-Iminomethyl-8-azabicyclo-[3.2.1]oct-3-yl)-2methylbenzo[b]thiophene-3-carboxylate hydrochloride (Compound 24)

endo-(8-Iminomethyl-8-azabicyclo-[3.2.1]oct-3-yl)-3,5-dimethylbenzoate hydrochloride (Compound 25)

M.p. 252°–253° C. (Acetone/EtOH)
Analysis;
Found % C 62.86, H 7.03, N 8.54,
C$_{17}$H$_{22}$N$_2$O$_2$·HCl;
Calc. % C 63.24, H 7.18 N 8.68.

endo-N-(8-Iminomethyl-8-azabicyclo-[3.2.1]oct-3-yl)-3,5-dimethylbenzamide hydrochloride (Compound 26)

M.p. 80°–82° C.
Analysis;
Found % C 63.01, H 7.48, N 12.97,
C$_{17}$H$_{23}$N$_3$O·HCl;
Calc. % C 63.44, H 7.52, N 13.05.

endo-(9-Iminomethyl-9-azabicyclo[3.3.1]non-3-yl)-1H-indole3-carboxylate hydrochloride (Compound 27)

M.p.>270° C.
Analysis;
Found % C 61.73, H 6.31, N 11.84,
C$_{18}$H$_{21}$N$_3$O$_2$·HCl;
Calc. % C 62.16, H 6.37, N 12.08.

endo-(8-Iminomethyl-8-azabicyclo-[3.2.1]oct-3-yl)quinoline3-carboxylate dihydrochloride (Compound 28)

M.p. 261°–262° C. (EtOH)
Analysis;
Found % C 56.01, H 5.61, N 10.89,
C$_{18}$H$_{19}$N$_3$O$_2$·HCl;
Calc. % C 56.55, H 5.54, N 10.99.

endo-[8-(N-Ethylimino)methyl-8-azabicyclo-[3.2.1]oct-3-yl]1H-indole-3-carboxylate hydrochloride (Compound 29)

a) Ethylisothiocyanate (0.46 g) dissolved in THF (5 ml) was added to a suspension of endo-(8-azabicyclo[3.2 1 ]oct-3-yl)-1H-indole-3-carboxylate (1.3 g) in THF (30 ml). The reaction mixture was stirred for 4 hours and a clear solution was obtained. 1.4 g of endo-[8-(N-ethyl thiocarbamoyl)-8-azabicyclo[3.2.1]oct-3-yl]-1H-indole-3-carboxylate were obtained M.p. 230°–232° C.

Analogously the following intermediates were obtained: 4-Amino-5-chloro-2-methoxy-N-[N'-(N''ethylthiocarbamoyl)-2-aminoethyl]benzamide. M.p. 168°–170° C. endo-N-[9-(N'-Methilthiocarbamoyl)-9-azabicyclo[3.3.1]non-3-yl]-1-methyl-indazole-3carboxamide. M.p. 190° C. endo-N-[8-(N'-Methilthiocarbamoyl)-8-azabicyclo[3.2.1]oct-3-yl]-1H-indol-3-carboxamide. M.p.>270° C.

The same product was also prepared by reacting 1H-indol-3-carbonylchloride with endo-8-(N-methyl thiocarbamoyl)-8-azabicyclo-[3.2.1]octan-3-amine in THF in the presence of triethylamine.

b) 0.8 g of endo-[8-(N-ethyl thiocarbamoyl)-8-azabicyclo-[3.2.1]oct-3-yl]-1H-indol-3-carboxylate were dissolved in a mixture of absolute ethanol (10 ml) and CH$_2$Cl$_2$ (100 ml). Ni/Raney (4.0 g) was added to the resulting solution, under stirring and at room temperature, and stirring was kept on for 5 hours. After filtering the clear solution was concentrated to dryness and the raw product was crystallized from acetonitrile. 0.17 g of the desired product were obtained. M.p.>270° C.

Analysis;
Found % C 62.71, H 6.73, N 11.51,
$C_{19}H_{23}N_3O_2 \cdot HCl$;
Calc. % C 63.06, H 6.68, N 11.61.

Analogously the following compounds can be obtained:

endo-[8-(N-Methylimino)methyl-8-
-azabicyclo-[3.2.1]oct-3-yl]indazole-carboxylate hydrochloride (Compound 30)

endo-N-[8-(N'-Methylimino)methyl-8-azabicyclo-[3.2.1]oct-3-yl]-1H-indol-3-carboxamide hydrochloride (Compound 31)

M.p. 126°-129° C. (acetone)
Analysis;
Found % C 61.86, H 6.80, N 15.93,
$C_{18}H_{22}N_4O \cdot HCl$;
Calc. % C 62.32, H 6.68, N 16.15.

4-Amino-5-chloro-2-methoxy-N-[N'-(N''-ethyliminomethyl)2-aminoethyl]benzamide hydrochloride (Compound 32)

M.p. 165°-170° C. (dec)
Analysis;
Found % C 45.97, H 6.09, N 16.01,
$C_{13}H_{19}ClN_4O_2 \cdot HCl$;
Calc. % C 46.58, H 6.01, N 16.71.

EXAMPLE 19

[1-(1'-Iminoethyl)-piperidin-4-yl]-1H-indol-3-carboxylate hydrochloride (Compound 33)

Ethyl acetoimidate hydrochloride (1.2 g) was added portionwise to a solution of (piperidine-4-yl)-1H-indole-3-carboxylate (2 g) in ethanol (300 ml). The reaction mixture was stirred at room temperature for 3 hours. After evaporation of the solvent the residue was chromatographed on silica (eluent n.propanol, acetic acid, $H_2O$ 90:10:10). After treatment of the base with HCl the title compound, as hydrochloride, was obtained (0.4 g). M.p. 240° C.

Analysis;
Found % C 59.60, H 6.28, N 12.97,
$C_{16}H_{19}N_3O_2 \cdot HCl$;
Calc. % C 59.71, H 6.26, N 13.06.

Analogously the following compounds can be obtained:

endo-[8-(1-Iminoethyl)-8-azabicyclo-[3.2.1]oct-3-yl]-3,5-dichlorobenzoate hydrochloride (Compound 34)

4-Amino-5-chloro-2-methoxy-N-[1-(1'-iminoethyl)pyrrolidin-2-yl-methyl]benzamide hydrochloride (Compound 35)

endo-8-(1'-Iminoethyl)-8-azabicyclo-[3.2.1]oct-3-yl]-1H-indol-3-carboxylate hydrochloride (Compound 36)

1-(1'-Imino-n-propyl)-piperidin-4-yl]-1H-indole-3-carboxylate hydrochloride (Compound 37)

This compound was prepared analogously to compound 33 using (piperidin-4-yl)-3,5-dimethylbenzoate and ethyl propionimidate hydrochloride in absolute ethanol. After chromatographing on Silicagel (eluent $CH_2Cl_2$/methanol/acetic acid 80:15:15) the title compound was obtained.

M.p. 70°-75° C. (Freeze-dried).
Analysis;
Found % C 60.04, H 6.56, N 12.36,
$C_{17}H_{21}N_3O_2 \cdot HCl$;
Calc. % C 60.80, H 6.60, N 12.51.

EXAMPLE 20

[1-[1'-(N-Methylimino)ethyl]piperidin-4-yl-3,5-dimethylbenzoate hydrochloride (Compound 38)

Phenyl-N-methylacetimidate (0.6 g) was added to a solution of (piperidin-4-yl)-3,5-dimethylbenzoate hydrochloride (1.0 g) in absolute ethanol (10 ml) and the solution was stirred at room temperature for 4 hours. After concentrating to dryness the product was chromatographed on Silicagel (eluent methylene dichloride/methanol/acetic acid 7:2:1). Yield 0.35 g M.p. 68°-72° C. (Freeze-dried)
Analysis;
Found % C 62.31, H 7.81, N 8.63,
$C_{17}H_{24}N_2O_2 \cdot HCl$;
Calc. % C 62.85, H 7.76, N 8.62.

The following not limitative examples of pharmaceutical compositions according to the invention are reported:

EXAMPLE 21

Tablets active ingredient 25 mg
lactose 311 mg
corn starch 60 mg
magnesium stearate 4 mg Method of preparation: The active ingredient, lactose and corn starch were mixed and homogeneously moistened with water. After screening of the moist mass and drying in a tray drier, the mixture was again passed through a screen and magnesium stearate was added. Then the mixture was pressed into tablets weighing 400 mg each. Each tablet contains 25 mg of active ingredient.

EXAMPLE 22

Capsules active ingredient 25 mg
lactose 223 mg
magnesium stearate 2 mg

Method of preparation: The active ingredient was mixed with auxiliary products, and the mixture was passed through a screen and mixed homogeneously in a suitable device. The resulting mixture was filled into hard gelatine capsules (250 mg per capsule); each capsule contains 25 mg of active ingredient.

EXAMPLE 23

Ampoules

Active ingredient 5 mg
sodium chloride 9 mg

Method of preparation: The active ingredient and sodium chloride were dissolved in an appropriate amount of water for injection. The resulting solution was filtered and filled into ampoules under sterile conditions. Each ampoule contains 5 mg of active ingredient.

EXAMPLE 24

Suppositories active ingredient 25 mg
semisynthetic gliceride of fatty acids 925 mg Method of preparation: The semisynthetic glycerides of fatty acids were melted and the active ingredient was added while stirring homogeneously. After cooling at a proper temperature the mass was poured into preformed moulds for suppositories weighing 950 mg each. Each suppository contains 25 mg of active ingredient.

EXAMPLE 25

Oral drops active ingredient 5 mg
sorbitol 350 mg
propylene glycol 100 mg
citric acid 1 mg
sodium citrate 3 mg
demineralized water q.s. 1 ml Method of preparation: The active ingredient, citric acid and sodium citrate were dissolved in a mixture of a proper amount of water and propylene glycol. Then sorbitol was added and the final solution was filtered. The solution contains 0.5% of active ingredient and is administered by using a proper dropper.

What is claimed is:

1. Compound of general formula (I)

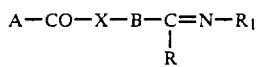   (I)

wherein
A is

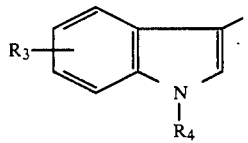

wherein
$R_3$ is H, halogen, $C_{1-6}$ alkoxy
$R_4$ is H, $C_{1-6}$ alkyl
X is —O— or —NH—
B is a group selected from

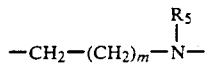   (a)

-continued

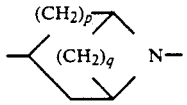   (b)

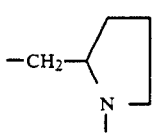   (c)

wherein
m is 1, 2
p is 0, 1, 2,
q is 0, 1, 2, 3
$R_5$ is H, $C_{1-6}$ alkyl
R is H, $C_{1-6}$ alkyl optionally substituted by halogen, $NR_6R_7$ in which $R_6$ is H, $C_{1-6}$ alkyl, $NO_2$, CN and $R_7$ is H, $C_{1-6}$ alkyl;
$R_1$ is H, $C_{1-6}$ alkyl optionally substituted by halogen, CN, or tautomers thereof, optical isomers thereof and acid addition salts thereof.

2. The compound as recited in claim 1, wherein A is 3-linked 1H-indol, and
B is

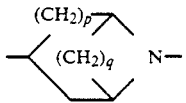

3. The compound [Endo-8-iminomethyl-8-azabicyclo[3.2.1]-1H-indole-3-carboxylate, hydrochloride as recited in claim 1.

4. The physiologically acceptable acid addition salt of a compound as recited in claim 1.

5. The physiologically acceptable acid addition salt as recited in claim 4 wherein the physiologically acceptable acid is hydrochloric, sulphuric, hydrobromic, acetic, citric or tartanic.

6. A pharmaceutical composition comprising an effective amount of a compound as recited in claim 1 and a pharmaceutically acceptable carrier.

7. A method for treating a warm-blooded animal suffering from motion sickness, migrain, cluster headaches, anxiety or psychosis which comprises administering to said animal a therapeutically effective amount of a compound as recited in claim 1.

8. A method for treating a warm-blooded animal suffering from chemotherapy or radiation-induced nausea or emesis or from delayed gastric emptying or gastrointestinal motility disorders which comprises administering to said animal a therapeutically effective amount of a compound as recited in claim 1.

* * * * *